June 1, 1965 A. P. HOWARD Plant Pat. 2,523
ROSE PLANT
Filed Nov. 4, 1963
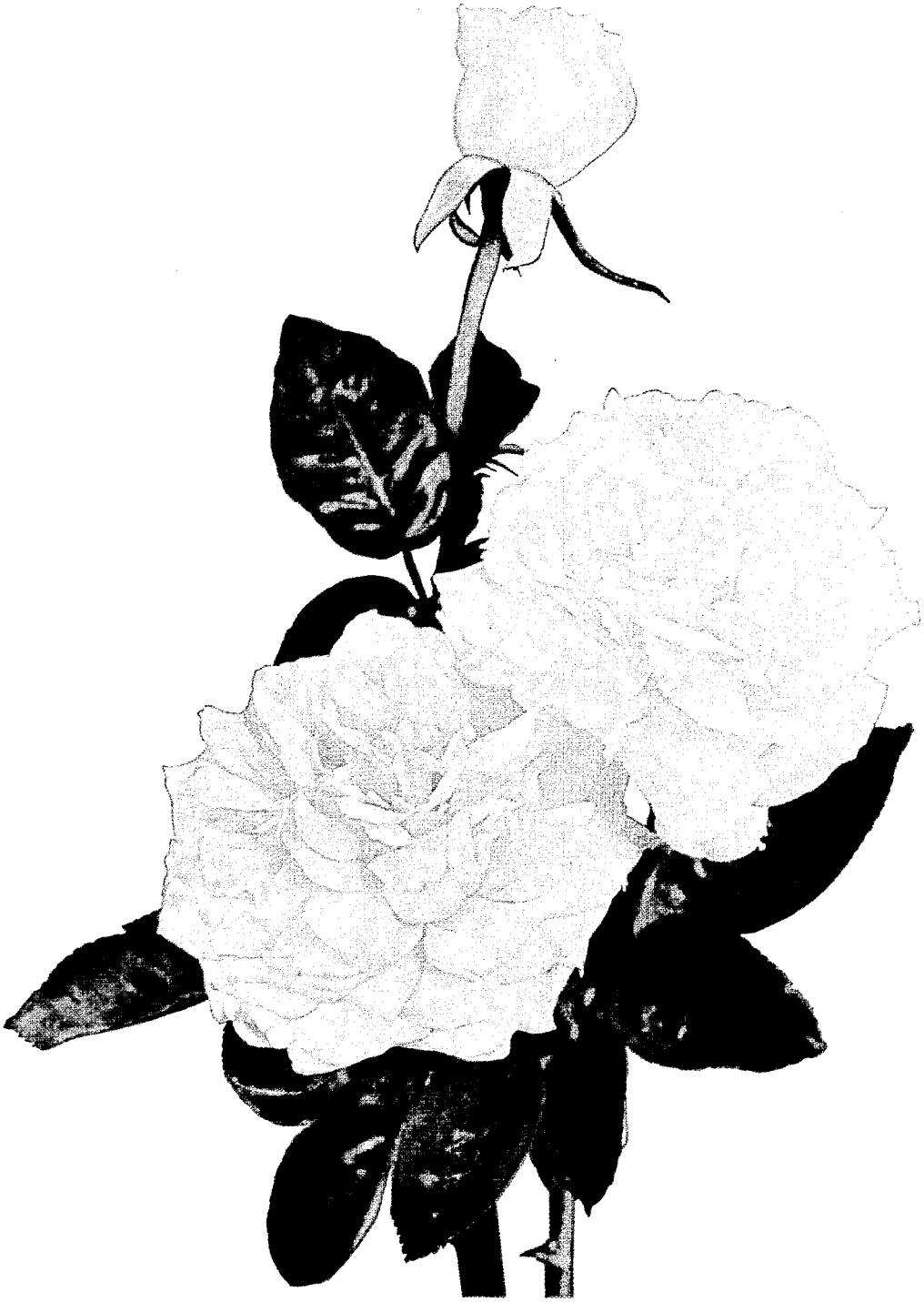
INVENTOR
ARTHUR P. HOWARD
BY J. F. Cuneo
ATTORNEY United States Patent Office Plant Pat. 2,523
Patented June 1, 1965

2,523
ROSE PLANT

Arthur P. Howard, Sierra Madre, Calif., assignor to Great Western Rose Company, Inc., Pomona, Calif., a corporation of California Filed Nov. 4, 1963, Ser. No. 327,860
1 Claim. (Cl. Plt.—11)

This invention relates to a new and distinct variety of rose plant which falls in the hybrid tea rose class.

This plant resulted from the cross-breeding of Peace, a patented variety, United States Patent No. 591, and an unnamed yellow seedling, an unpatented variety, after numerous experiments conducted by me in Montebello, county of Los Angeles, State of California. The original plant was produced by me in 1955, the seed parent was Peace and the pollen parent was the unnamed yellow rose.

The flowers that are produced by the new variety of rose plant are unique in that they are a deep yellow with scarlet tips. The blooms are double and of large size and are produced at the end of long stems. The flowers are produced in abundance during the growing season that extends from April to the end of November. The blooms have a fruity fragrance that is quite pronounced.

In comparing the blooms of my new variety with those of its seed parent Peace, the flowers are buff yellow with scarlet tips whereas those of the parent plant are basically pink and rose shading toward mauve. Compared to its pollen parent, the unnamed yellow seedling, the flowers are tinged with scarlet and are basically an orange buff whereas those borne by the pollen parent are yellow. The flowers of the new variety are carried on long stems and are larger than those of either of its parent plants.

The new rose belongs to the outdoor bush type and is used principally for cut flowers and for garden ornamentation. The plant has been reproduced asexually by budding performed at Montebello, California. The plants and flowers reproduce true with all their distinguishing characteristics, and these distinguishing features have been transmitted through succeeding propagations of the variety. The plant will not reproduce true from seed.

The accompanying illustrations in color show a typical specimen of the flowers and foliage. These colors are as correct as it is possible to reproduce them by the type of representation used.

A detailed description of the new variety of rose follows, and to facilitate identification of the important colors described in this specification, the designations adopted by the British Horticultural Colour Charts have been followed.

The new rose belongs to the outdoor bush type and is a member of the so-called hybrid tea rose class. Its scarlet orange flowers with extremely long stems are particularly desirable as cut flowers and the plant is an asset to any garden.

*The flower*

Locality where grown and observed: Montebello, California; Temple City, California; Pomona, California; and La Puente, California.

Flowers borne: Singly on stems eighteen to twenty-four inches long.

Number of blooms: When grown outdoors the plant produces about fifteen blooms on a plant at any given time.

Continuity: Blooms continuously throughout the flowering season that in the coastal region of southern California normally extends from April through November. Maximum flowing occurs during the months of April, May, and June and again in September, October, and November.

Fragrance: The flowers have a fruity fragrance which is very pronounced for this color of rose.

Bud:

*Peduncle.*—Length—about three inches. Color—olive green with a coppery overtone.

*Before calyx breaks.*—Size—between one and one and one quarter inches. Form—high centered and conical.

*As calyx breaks.*—Color—orange to light orange. Sepals—large, being usually 1½″ by ½″, having a light green color inside and a darker green outside.

*As first petal opens.*—Size—approximately one and one half by one and one half inches. Color—tip has a slight indication of Jasper Red o18/3; base and major portion of petal is Majolica Yellow o9/1. Form—orbicular or ovate with margin straight and entire. Opening—open up normally and is not particularly affected by cold, hot, wet or dry atmospheric conditions.

Bloom:

*Size.*—Average flower is from 4″ to 4½″ when fully opened. Some flowers have been observed that would be approximately 6″ across.

*Petalage.*—Number of petals average eighty, and are arranged regularly.

*Form.*—High centered and globular when first becoming fully opened. The inner petals vary in size and are smaller than the outer petals.

*Petals.*—Texture—petals have a waxy appearance and are fairly thick. Shape—all petals are orbicular and have a good aspect; the edges are entire and are normally not reflexed.

(This description of a newly opened flower was taken from observations made on a rose grown in the Pomona area and observed in the month of October.)

*Color.*—Tip—Jasper Red o18/3. Principal portion and base—Majolica Yellow o9/1. (The colors are the same for all petals.)

The flower has the general characteristics hereinafter set forth:

*General color effect.*—The general color appearance could be described as light buff yellow when the flower is viewed as a whole. In normal climatic conditions the colors do not change appreciably, but unusual heat will cause the colors to diminish in intensity.

*Behavior.*—Petals drop off clean. Petals are persistent and are not inordinately affected by hot, cold, dry or wet atmospheric conditions.

*Flower longevity.*—Roses will remain in good condition from five to seven days while on the bush; after the flowers are cut they will usually last about five days.

*Reproductive organs*

Stamens: Average in number.

Filaments: These are of medium length, about ¼″ in length.

Anthers: Anthers are not prominent.

Pollen: moderate quantity. Color—golden yellow.

Pistils: Pistils are numerous.

Styles: The styles are moderately even; average length being about ¼″.

Stigma: Not prominent.

Ovaries: Ovaries are usually enclosed in calyx.

Hips:

*Length.*—Average in length.

*Form.*—Ovoid generally, approximately ⅜″ by ⅜″.

*Color.*—Dark green outside with the inside somewhat lighter green.

Seeds: The seeds are of average size but do not set freely.

*The plant*

Foliage:

*Leaves.*—Compound of an average of five leaflets; spaced about four inches apart. Leaves are leathery and glossy with edges slightly serrated. Shape—ovate with end coming to a point. Size—one and three quarter inches by one and one quarter inches. Color—Parsley Green oo962/1 on upper side and Willow Green ooo862/1 on the underside.

*Leaflets.*—Shape—ovate with apex pointed. Color—mature leaves—upper side is Parsley Green oo962/1 with the lower side Willow Green ooo862/1; young leaves—have approximately the same color as mature leaves but have a definite reddish cast.

*Type.*—Imparipinnate.

*Stipules.*—Stipules are about one half inch in length.

Growth:

*Habit.*—Upright and well branched. Plant grows from four to five feet in height and is hardy and vigorous.

*Canes.*—½″ to ¾″ in diameter after plant has become established.

*Main stems.*—The main stems are from 18″ to 24″ in length and are robust. Color: best described as coppery green and bronze.

*Prickles.*—Though a few are observed they are quite small being about 1/16″ in length. They are widely spaced and are slightly reclining. Color—dark brown. Hair—none.

*Small prickles.*—None.

*Branches.*—Color—bronze colored. Shape—predominantly vertical. Hair—none. Small prickles—none.

*New shoots.*—Color—same as mature growth but more maroon. Large prickles—scarcely noticeable. Small prickles—none.

Having described my invention, I claim:

The new and distinct variety of rose plant of the class designated as hybrid tea roses, substantially as herein shown and described, characterized particularly as to novelty by the unusual red-yellow flowers borne on long stems, the strong fruity fragrance of the flowers, the coppery colored stems, the small number of prickles, the longevity of the flowers after they have been cut, and the vigorous upright growth of the plant.

No references cited.

ABRAHAM G. STONE, *Primary Examiner.*